United States Patent [19]
Beck et al.

[11] Patent Number: 6,133,470
[45] Date of Patent: *Oct. 17, 2000

[54] INTEGRATION OF P-XYLENE PRODUCTION AND SUBSEQUENT CONVERSION PROCESS

[75] Inventors: Jeffery S. Beck, Burlington; David L. Stern, Mount Laurel, both of N.J.

[73] Assignee: Mobil Oil Corporation, Fairfax, Va.

[*] Notice: This patent issued on a continued prosecution application filed under 37 CFR 1.53(d), and is subject to the twenty year patent term provisions of 35 U.S.C. 154(a)(2).

[21] Appl. No.: 09/123,281

[22] Filed: Jul. 28, 1998

[51] Int. Cl.⁷ .......................... C07C 67/39; C07C 51/265
[52] U.S. Cl. .......................... 560/77; 562/409; 562/412; 562/413
[58] Field of Search ................ 560/77; 562/409, 562/412, 413

[56] References Cited

U.S. PATENT DOCUMENTS

| | | | |
|---|---|---|---|
| Re. 31,782 | 12/1984 | Olson et al. | 585/481 |
| 2,833,816 | 5/1958 | Saffer et al. | 260/524 |
| 4,705,909 | 11/1987 | Yan | 585/828 |
| 5,243,117 | 9/1993 | Chang et al. | 585/467 |
| 5,321,183 | 6/1994 | Chang et al. | 585/475 |
| 5,349,113 | 9/1994 | Chang et al. | 585/475 |
| 5,349,114 | 9/1994 | Lago et al. | 585/475 |
| 5,365,003 | 11/1994 | Chang et al. | 585/470 |
| 5,365,004 | 11/1994 | Beck et al. | 585/475 |
| 5,367,099 | 11/1994 | Beck et al. | 585/475 |
| 5,403,800 | 4/1995 | Beck et al. | 502/64 |
| 5,406,015 | 4/1995 | Beck et al. | 585/475 |
| 5,475,179 | 12/1995 | Chang et al. | 585/475 |
| 5,476,823 | 12/1995 | Beck et al. | 502/60 |
| 5,488,194 | 1/1996 | Beck et al. | 585/475 |
| 5,495,059 | 2/1996 | Beck et al. | 585/470 |
| 5,498,814 | 3/1996 | Chang et al. | 585/475 |
| 5,516,736 | 5/1996 | Chang et al. | 502/64 |
| 5,552,357 | 9/1996 | Lago et al. | 502/63 |
| 5,567,666 | 10/1996 | Beck et al. | 502/71 |
| 5,569,805 | 10/1996 | Beck et al. | 585/446 |
| 5,571,768 | 11/1996 | Chang et al. | 502/64 |
| 5,602,066 | 2/1997 | Beck et al. | 502/64 |
| 5,612,270 | 3/1997 | Beck et al. | 502/64 |
| 5,625,103 | 4/1997 | Abichandani et al. | 585/475 |
| 5,625,104 | 4/1997 | Beck et al. | 585/475 |
| 5,633,417 | 5/1997 | Beck et al. | 585/475 |
| 5,659,098 | 8/1997 | Beck et al. | 585/475 |
| 5,675,047 | 10/1997 | Beck et al. | 585/467 |

FOREIGN PATENT DOCUMENTS

| | | |
|---|---|---|
| 727989 | 4/1955 | United Kingdom . |
| 809730 | 3/1959 | United Kingdom . |
| WO 93/17987 | 9/1993 | WIPO . |

OTHER PUBLICATIONS

J.J. Jeanneret, "UOP Parex Process", in *Handbook of Petroleum Refining Processes*, R.A. Meyers, ed., McGraw–Hill, New York 1997, pp. 2.45–2.53.

*Primary Examiner*—Michael G. Ambrose

[57] ABSTRACT

A process for producing terephthalic acid and/or dimethyl terephthalate includes contacting a toluene-containing reaction stream with a first catalyst under toluene disproportionation conditions to produce an intermediate product stream of para-xylene with negligible ortho-xylene. The first catalyst includes a crystalline molecular sieve which has an ortho-xylene diffusion rate of at least 50 minutes. The first catalyst can be modified by selectivation with a silicon compound or carbon compound. The intermediate product stream, without need for para-xylene purification, is oxidized to terephthalic acid or dimethyl terephthalate.

10 Claims, No Drawings

INTEGRATION OF P-XYLENE PRODUCTION AND SUBSEQUENT CONVERSION PROCESS

The invention relates to a process integrating p-xylene production with terephthalic acid and/or dimethyl terephthalate production without need for intermediate purification of p-xylene

BACKGROUND OF THE INVENTION

Para-xylene is oxidized to produce terephthalic acid or dimethyl terephthalate which are polymerized to yield polyester fibers and films. Processes for the production of terephthalic acid (1,4-benzenedicarboxylic acid) and dimethyl terephthalate are well known and described, e.g., in U.S. Pat. No. 2,833,816 and British Patent Specification Nos. 809,730 and 727,989.

Of the three xylene isomers, meta, ortho and para, only p-xylene is suitable for the production of terephthalic acid and/or dimethyl terephthalate for polyester manufacture because of the ability of p-xylene to form straight polymer chains. Straight claims are necessary to give polyester its fiber-forming or film-forming characteristics and high tensile strength.

The p-xylene must be substantially pure to avoid unwanted side reactions when the p-xylene is oxidized to terephthalic acid.

Para-xylene has been typically produced by methylation of toluene, e.g., by reaction of toluene with methanol as generally described by Chen et al., *J. Am. Chem. Soc.* 1979, 101:6783, and by toluene disproportionation, e.g., as generally described by Pines in *The Chemistry of Catalytic Hydrocarbon Conversions*, Academic Press, New York 1981, p. 72. Such methods typically produce a mixture of $C_8$ products including para-xylene, ortho-xylene, meta-xylene and ethylbenzene. Para-xylene may be recovered from mixed $C_8$ streams followed by xylene isomerization of the remaining stream as described, e.g., in U.S. Pat. Nos. 3,856,871 and Re 31,782.

In terephthalic acid production, one unwanted by-product results from the presence of o-xylene in the xylene feed. Any o-xylene present is oxidized to orthophthalic acid and subsequently dehydrated to phthalic anhydride, interfering with terephthalic acid production and impacting on the oxidation catalyst lifetime. If ethylbenzene (EB), another $C_8$, is present in the p-xylene feed for terephthalic and production, the EB may be oxidized to benzoic acid. Meta-xylene is oxidized to isophthalic acid. These oxidation products are more easily separated from PTA than the oxidation products of o-xylene. The quality of polyester is affected by even small amounts of organic or inorganic impurities which cause process difficulties during polymerization and affect the color, thermal and photochemical stability, and long-term durability of the polyester product. The precursor for polyester production is purified terephthalic acid (PTA). Further, the PTA thus produced may be esterified with an alcohol, e.g., reaction of PTA with methanol yields dimethyl terephthalate which may also be used in polyester production.

As disclosed, e.g., in British Patent Specification No. 727,989, if the initial p-xylene feed does not consist of pure para-xylene compound but also contains other xylene isomers and/or non-aromatic compounds, a purification of the feed is necessary. Purification of the p-xylene feed is generally carried out using physical processes such as fractional distillation or crystallization described, e.g., in U.S. Pat. Nos. 3,177,255 and 3,467,724, absorption described, e.g., in U.S. Pat. No. 2,985,589, or chemical processes, e.g., contacting with formaldehyde in acid solution which removes m-xylene as a resin. A widely used method is UOP's PAREX® process described by J. J. Jeanneret, "UOP Parex Process," in *Handbook of Petroleum Refining Processes*, R. A. Meyers, ed., McGraw - Hill, New York 1997. Other methods for separating p-xylene from a $C_8$ aromatic mixture are described by U.S. Pat. No. 4,705,909 and references cited therein. In conventional xylene manufacture, significant costs are incurred for p-xylene purification for PTA production.

It is an object of the invention to improve terephthalic acid and/or dimethyl terephthate manufacture by minimizing unwanted oxidation by-products. It is another object of the invention to eliminate the need for a purification process for p-xylene to be used in terephthalic acid and/or dimethyl terephthalate production.

SUMMARY OF THE INVENTION

A process for producing terephthalic acid (TPA) includes integration of p-xylene production with oxidation of the p-xylene to produce terephthalic acid. The TPA thus produced may also be esterified, e.g., to dimethyl terephthalate in the same or separate reactor.

In the first segment of production, hydrocarbon feedstream including toluene is first contacted under toluene disproportionation conditions, with a first catalyst which includes a catalytic molecular sieve selective for para-xylene production. The first catalyst includes a crystalline molecular sieve which preferably has a diffusion rate for ortho-xylene of at least 50 minutes to sorb o-xylene in an amount equal to 30% of the equilibrium sorption capacity for xylenes at 120° C. and at a xylene partial pressure of 4.5±0.8 mm of mercury. Suitable crystalline molecular sieves for the first catalyst include zeolites, SAPO's and $ALPO_4$'s.

In a preferred embodiment the first catalyst includes a crystalline molecular sieve which has been selectivated through silicon selectivation using ex situ methods of impregnation, multiple impregnation, or in situ methods of trim selectivation; coke selectivation; or combinations of these. The first catalyst may be self-bound, may include a silica binder, may include a binder that has no intentionally added alumina or may be a zeolite bound zeolite.

The first catalyst also preferably includes incorporated metal, preferably platinum, palladium, silver, gold, zinc, gallium, copper, nickel, rhodium, iridium, cobalt, iron, ruthenium, manganese, rhenium, tungsten, molybdenum, chromium or combinations thereof.

The first contacting produces an intermediate product stream containing p-xylene with negligible or essentially no ortho-xylene and negligible or essentially no ethylbenzene (EB). The intermediate product stream containing p-xylene is oxidized to terephthalic acid in a second contacting with a second catalyst. There is no need for purification of the intermediate product stream to remove ortho-xylene or EB. The second catalyst is any catalyst which catalyzes oxidation of p-xylene to terephthalic acid, e.g., heavy metal catalyst such as cobalt and/or manganese, and which optionally may include a catalyst for esterification to dimethyl terephthalate.

Advantageously, a costly xylene separation step is eliminated and the product stream of the first contacting can be directly integrated with the oxidation process to pure terephthalic acid or dimethyl terephthalate.

DETAILED DESCRIPTION OF THE INVENTION

Catalyst System

Catalysts useful for the production of p-xylene in this invention may comprise crystalline molecular sieves having the specified ortho-xylene diffusion rate, e.g., zeolites, ALPO$_4$'s, SAPO's or combinations of these.

Examples of crystalline molecular sieves useful in this invention include intermediate pore size zeolites ZSM-5 (U.S. Pat. Nos. 3,702,886 and Re,29,948); ZSM-11 (U.S. Pat. No. 3,709,979); ZSM-12 (U.S Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046, 685); and ZSM-58 (U.S. Pat. No. 4,417,780). Also useful are silicoaluminophosphates (SAPO's), particularly SAPO-5 and SAPO-11 (U.S. Pat. No. 4,440,871) and aluminophosphates (ALPO$_4$'s), particularly ALPO$_4$-5, and ALPO$_4$-11 (U.S. Pat. No. 4,310,440). The entire contents of the above references are incorporated by reference herein. Intermediate pore size zeolites generally have a Constraint Index within the approximate range of 1 to 12 (e.g., zeolites having less than about 7 Angstroms pore size, such as from about 5 to less than about 7 Angstroms). Preferred intermediate pore zeolites include ZSM-5, ZSM-11, ZSM-12, ZSM-35 and MCM-22. More preferred is ZSM-5, preferably having a silica to alumina molar ratio of at least about 5, preferably at least about 10, more preferably at least 20. The silica to alumina ratio may be determined by conventional analysis. This ratio is meant to represent, as closely as possible, the molar ratio in the rigid anionic framework of the zeolite crystal and to exclude silicon and aluminum in the binder or in cationic or other form within the channels.

A crystalline molecular sieve in bound or unbound form can be silicon selectivated through ex situ methods of impregnation or multiple impregnation or in situ methods of trim selectivation; or coke selectivated; or combination of these, to result in the desired ortho-xylene diffusion rate.

Multiple impregnation methods are described, e.g., in U.S. Pat. Nos. 5,365,004, 5,367,099, 5,382,737, 5,403,800, 5,406,015, 5,476,823, 5,495,059, 5,633,417. Other ex situ selectivations are described in U.S. Pat. Nos. 5,574,199 and 5,675,047. Trim selectivation is described, e.g., in U.S. Pat. Nos. 5,321,183, 5,349,113, 5,475,179, 5,498,814, 5,607, 888. Other silicon selectivations are described, e.g., in U.S. Pat. Nos. 5,243,117, 5,349,114, 5,365,003, 5,371,312, 5,455,213, 5,516,736, 5,541,146, 5,552,357, 5,567,666, 5,571,768, 5,602,066, 5,610,112, 5,612,270, 5,625,104, 5,659,098. Coke selectivation is described in U.S. Pat. Nos. 5,234,875; 4,581,215; 4,508,836; 4,358,395; 4,117,026; and 4,097,543. All of these patents describing selectivation are incorporated by reference herein.

When ZSM-5 is used as the toluene conversion catalyst of this invention, it may comprise a medium or large crystal size. If another intermediate pore size zeolite is used as the toluene conversion catalyst, the crystal size may need to be adjusted from those given above for best performance.

Procedures for preparing silica bound ZSM-5 are described in U.S. Pat. Nos. 4,582,815; 5,053,374; and 5,182, 242, incorporated by reference herein. A particular procedure for binding ZSM-5 with a silica binder involves an extrusion process.

The catalyst may be a zeolite bound zeolite as described in U.S. Pat. No. 5,665,325.

A particular process for preparing silica bound ZSM-5 may comprise the steps of:

(i) mulling and then extruding a mixture comprising water, ZSM-5, colloidal silica and sodium ions under conditions sufficient to form an extrudate having an intermediate green strength sufficient to resist attrition during ion exchange step (ii) set forth hereinafter;

(ii) contacting the uncalcined extrudate of step (i) with an aqueous solution comprising ammonium cations under conditions sufficient to exchange cations in said ZSM-5 with ammonium cations; and (iii) calcining the ammonium exchanged extrudate of step (ii) under conditions sufficient to generate the hydrogen form of said ZSM-5 and increase the crush strength of said extrudate.

Another method of silica binding uses a suitable silicone resin, e.g., a high molecular weight, hydroxy functional silicone, such as Dow Corning Q6-2230 silicone resin in a method disclosed in U.S. Pat. No. 4,631,267, incorporated by reference herein. Other silicone resins that may be used in the method of this invention include those described in U.S. Pat. No. 3,090,691. When a silicone resin is used, a suitable polar, water soluble carrier, such as methanol, ethanol, isopropyl alcohol, N-methyl pyrrolidone or a dibasic ester may also be used along with water as needed. Dibasic esters that may be useful in this invention include dimethyl glutarate, dimethyl succinate, dimethyl adipate, and mixtures thereof, one example of which is DuPont Chemical Co. DBE, which typically comprises about 50 to 75 percent dimethyl glutarate, 10 to 25 percent dimethyl adipate, 19 to 26 percent dimethyl succinate and less than about 0.2 wt. % methanol.

Extrusion acids may also be useful in the preparation of the catalysts of this invention. Methyl cellulose is a suitable extrusion aid, and one particular methyl cellulose that is effective as an extrusion aid in the method of this invention is a hydroxypropyl methyl cellulose, such as K75M Methocel™, available from Dow Chemical Co. Methyl cellulose may also be used alone or in combination with other binder or matrix material as a burn-out material to increase the porosity of the catalysts.

There are various methods for increasing the selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound"). Also, U.S. Pat. Nos. 5,367,099; 5,382,737; 5,365,004; 5,403,800; 5,406, 015; and 5,476,823 disclose methods for silicon selectivation of catalysts and use of those catalysts in toluene and ethylbenzene disproportionation. These patents are incorporated by reference herein.

In accordance with one selectivation method (first method), the multiple impregnation method, the catalyst is selectivated by one or more treatments with a liquid organosilicon compound in a liquid carrier, each treatment being followed by calcination of the treated material in an oxygen containing atmosphere, e.g., air. More particularly, for example, with reference to the above-mentioned steps (i)–(iii), this first selectivation method may involve the additional steps of:

(iv) contacting the calcined extrudate of step (iii) with a liquid comprising a liquid carrier and at least one organosilicon selectivating agent having at least two silicon atoms per molecule under conditions sufficient to incorporate said organosilicon selectivating agent in the extrudate.

(v) calcining the extrudate of step (iv) under conditions sufficient to decompose said organosilicon selectivating agent and to remove any residue of said liquid carrier from said extrudate; and, optionally, (vi) repeating selectivation steps (iv) and (v) at least once.

Another method (second method) for selectivating the catalyst, trim-selectivation, involves passing a feed stream comprising hydrogen and an aromatic (e.g., toluene) or a paraffin (e.g., hexane or decane) and an organosilicon compound over HZSM-5, e.g., silica bound ZSM-5, under conditions sufficient to deposit a residue of organosilicon compound on the ZSM-5.

The above-mentioned first method for selectivating the zeolite, wherein the zeolite, e.g., HZSM-5, is treated by multiple impregnation treatments, is referred to herein as the multiple impregnation method. The above-mentioned second method for selectivating the zeolite, wherein the zeolite, e.g., HZSM-5, is treated under trim-selectivation conditions, is referred to herein as the trim-selectivation method. Another method (third method) for selectivating the zeolite, described herein, which includes decomposing an organic compound on and in the zeolite, is referred to herein as the coke selectivation method. The present catalyst may be selectivated by any of the above selectivation methods or by more than one selectivation method used in combination.

In accordance with the multiple impregnation method, the zeolite, e.g., HZSM-5, is treated at least once, e.g., at least twice, e.g., 3 times or more, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. As mentioned above, the zeolite may be silica bound before selectivation, after selectivation, or between successive selectivation coatings.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation. When the catalyst is impregnated with an organosilicon compound included in an organic carrier, the organic carrier may be any organic compound or mixture of organic compounds which are capable of dissolving or otherwise suitably suspending the organosilicon compound. Such organic carriers may be hydrocarbons, such as linear, branched, and cyclic hydrocarbons having five or more, especially 7 or more, carbon atoms per molecule, e.g., alkanes such as heptane, octane, nonane, decane, undecane and dodecane. The boiling point of the organic compound, e.g., alkane, may be greater than about 70° C. Mixtures of low volatility organic compounds, such as hydrocracker recycle oil, may be employed as carriers. Particularly preferred organic carriers are decane and dodecane.

The organosilicon compound which is used to selectivate the zeolite may be a silicone, siloxane or a silane. Silicones are defined herein as those compounds wherein silicon atoms are bonded to one another via oxygen atoms. Silanes are defined herein as those compounds wherein silicon atoms are bonded directly to one another. The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000 and preferably within the approximate range of 150 to 10,000.

The kinetic diameter of the selectivating agent may be larger than the zeolite pore diameter, in order to avoid entry of the selectivating agent into the zeolite pores and any concomitant reduction in the internal activity of the zeolite. When a silicon compound is used that is of a size small enough to enter the pores of the catalyst crystal, it may be desirable to use the sodium form of the zeolite rather than the hydrogen form.

The silicone compound which may be used to selectivate the present zeolite may be considered to be constructed of a siloxy backbone structure capped with terminal groups. This siloxy backbone structure may be a chain structure represented by the formula

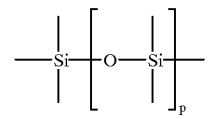

where p is from 1 to 100, e.g., 1 to 25 e.g., 1 to 9. This siloxy backbone structure may also be a cyclic structure represented by the formula.

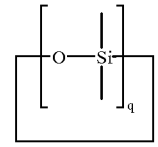

where q is from 2 to 10. Branched chain structures and composite chain/cyclic structures are also possible for the siloxy backbone of the silicone selectivating agent.

The hydrocarbyl groups which cap the available bonds of the siloxy backbone may have from 1 to 10 carbon atoms. Examples of such hydrocarbyl groups are methyl and phenyl.

Examples of silicone compounds having a chain siloxy backbone structure include those of the formula

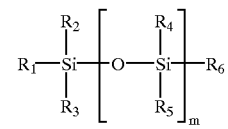

where $R_1$ and $R_6$ are independently hydrogen, methyl, or phenyl; $R_2$, $R_3$, $R_4$ and $R_5$ are independently methyl or phenyl; and m is from 1 to 100, e.g., from 1 to 25, e.g., from 1 to 10, e.g., from 1 to 4. Preferably, no more than one phenyl group is bonded to each silicon atom. Particular examples of such silicone compound having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetrasiloxane and decamethylcyclopentasiloxane. Particular examples of silicone compounds having a branched siloxy backbone structure are tris-(trimethylsiloxy)-phenylsilane and tris-(trimethylsiloxy)-silane.

The silane compounds, useful as selectivating agents according to the present method, may have structures corresponding to the above-mentioned silicone compounds, wherein the silicon atoms are bonded directly to one another instead of via oxygen atoms. Examples of silanes having a chain backbone structure include those of the formula

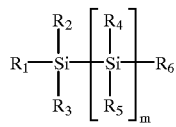

where $R_1$ and $R_6$ are independently hydrogen, methyl, or phenyl; $R_2$, $R_3$, $R_4$ and $R_5$ are independently methyl or phenyl; and m is from 1 to 100, e.g., from 1 to 25, e.g., from 1 to 10, e.g., from 1 to 4. An example of such a silane compound is hexamethyldisilane.

Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethylsilicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as $—N(CH_3)_3$, $—N(C_2H_5)_3$ and $—N(C_3H_7)_3$. A preferred water soluble organosilicon preselectivating agent is an n-propylamine silane, available as Hydrosil 2627 from Huls America. Particular water soluble organosilicon compounds, which may be used for multiple impregnations of the present catalyst, are referred to as amino silane polymers in U.S. Pat. No. 5,371,312, incorporated by reference herein. As mentioned previously herein, aqueous emulsions of organosilicon compounds comprising surfactants may be used for the impregnation of the present catalyst. Stable aqueous emulsion of organosilicon compounds (e.g., silicone oil) are described in U.S. Pat. No. 5,726,114, incorporated by reference herein.

The first catalyst may be selectivated by more than one selectivation method. In particular, prior to use in the present process, the crystalline molecular sieve may be contacted with an organosilicon compound, followed by calcination in an oxygen containing atmosphere. Such a pretreatment of the molecular sieve may also be referred to herein as a preselectivation treatment.

In accordance with an example of a preselectivation method, the catalyst is preselectivated by single or multiple treatments with a liquid organosilicon compound in a liquid carrier, each treatment being followed by calcination of the treated material in an oxygen containing atmosphere, e.g., air.

When the catalyst is preselectivated by a single or multiple impregnation technique, the catalyst is calcined after each impregnation to remove the carrier and to convert the liquid organosilicon compound to a solid residue material thereof This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the catalyst may be calcined at a rate of from about 0.2° C./minute to about 5° C./minute to a temperature greater than 200° C., but below the temperature at which the crystallinity of the crystalline molecular sieve is adversely affected. This calcination temperature may be below 700° C., e.g., within the approximate range of 350° C. to 550° C. the duration of calcination at the calcination temperature may be from 1 to 24 hours, e.g., from 2 to 6 hours.

The impregnated catalyst may be calcined in an inert or oxidizing atmosphere. An example of such an inert atmosphere is nitrogen, i.e., $N_2$, atmosphere. An example of an oxidizing atmosphere is an oxygen containing atmosphere, such as 30 air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the catalyst. The catalyst may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the molecular sieve or bound molecular sieve is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and the duration of the calcination. A suitable amount of silicon on the catalyst is greater than 9 weight percent, e.g., greater than 12 weight percent, exclusive of the silica present in the binder or in the crystalline molecular sieve itself.

After the impregnation/calcination sequence, the catalyst may be subjected to steaming conditions sufficient to increase or decrease the activity and/or selectivity of the catalyst, as desired. Such conditions are disclosed in U.S. Pat. No. 5,349,114, incorporated by reference herein. The steaming conditions may include a temperature of from about 100° C. to about 800° C., e.g., from about 175° C. to about 325° C., with from about 1% to about 100% steam, e.g., from about 50% to about 100% steam, at a pressure of from about 0.01 psia to about 5000 psia, e.g. from about 14 psia to about 50 psia, and for a duration of about 0.1 to about 200 hours, e.g., from about 0.5 to about 24 hours, e.g., from about 3 to about 6 hours. Excessive steaming or steaming under too severe conditions may be detrimental to the activity and selectivity of the catalyst.

In accordance with the trim-selectivation method described herein, the first catalyst may be contacted with a feed stream typically comprising hydrogen and an aromatic compound (e.g., toluene) or a paraffinic compound (e.g., hexane or decane) with the organosilicon compound under suitable trim selectivation conditions. These conditions may include a temperature ranging from about 100° C. to about 600° C., e.g., from about 300° C. to about 500° C., a pressure ranging from about 0 to about 2000 psig, e.g., from about 15 to about 800 psig, a mole ratio of hydrogen to hydrocarbons (e.g., toluene) from about 0.1 to 20 e.g., from about 0.25 to 10, e.g., from about 1 to about 4, and a wight hourly space velocity (WHSV) from about 0.1 to about 100 $hr^{-1}$, e.g., from about 0.1 to about 10 $hr^{-1}$. Toluene may comprise about 50 wt. % to 100 wt. %, e.g., at least 80 wt. % of the hydrocarbons in the feedstock. Other hydrocarbons, such as benzene, xylenes and trimethylbenzenes, may also be present in the trimselectivation feedstock.

The presence of a sufficient amount of hydrogen in the trim-selectivation feedstock is helpful to prevent rapid aging of the catalyst during the selectivation process, a small amount of carbonaceous deposit may form on the catalyst. As a result of this carbonaceous deposit, an elemental analysis of the trim-selectivated catalyst may reveal a carbon content significantly greater than the carbon content of the fresh catalyst prepared by the multiple impregnation method described herein. More particularly, the trim-selectivated catalyst may contain at least 2 wt. %, e.g., at least 4 wt. %, of carbon by elemental analysis, whereas the catalyst prepared by the multiple impregnation method may contain less than 0.5 wt. % of carbon as measured by elemental analysis. These weight percentages are expressed in terms of the weight of the entire catalyst including the crystalline molecular sieve, binder and optional components, such as hydrogenation/dehydrogenation components.

The first catalyst may also be subjected to controlled coking. This controlled coking procedure is also referred to herein as coke selectivation. this optional coke selectivation may involve contacting the catalyst with a thermally decomposable organic compound at an elevated temperature in excess of the decomposition temperature of said compound but below the temperature at which the crystallinity of the zeolite is adversely affected. This contact temperature may be, for example, less than about 650° C. The catalyst may be coked in a reactor or other vessel that is different than that used for the toluene conversion, followed by transport of the coked catalyst to the toluene conversion reactor.

Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. Nos. 4,117,026 and 5,476,823 incorporated by reference herein. An organosilicon cofeed may be, optionally, included along with the organic material feed used for coke selectivation. This organosilicon material may be selected from the organosilicon compounds mentioned hereinabove for use in the selectivation of the catalyst.

While it is not intended to be bound by any particular theory, it is possible that the selectivity of the present catalyst is obtained by producing changes in the diffusion properties of the zeolite that favor the desired reactions and inhibit undesired reactions.

The crystalline molecular sieve component of catalysts suitable for use as the first catalyst may be characterized by different xylene diffusion properties or xylene sorption capabilities. In particular, it has been found that the first catalyst should possess an equilibrium sorption capacity of xylene, which can be either para, meta, ortho or a mixture thereof, frequently para-xylene, since this isomer reaches equilibrium within the shortest time, of at least 1 gram per 100 grams of zeolite measured at 120° C. and a xylene pressure of 4.5±0.8 mm of mercury and an ortho-xylene sorption time for 30 percent of the xylene sorption capacity of greater than 50, preferably greater than 200, more preferably greater than 1200 (at the same conditions of temperature and pressure) are required in order to achieve the desired level of para-xylene selectivity at appropriate toluene conversion. The sorption measurements may be carried out gravimetrically in a thermal balance. The sorption test is described in U.S. Pat. Nos. 4,117,025; 4,159,282; 5,173,461; and Re. 31,782; each of which is incorporated by reference herein.

It has been found that zeolites exhibiting very high selectivity for para-xylene while minimizing ortho xylene require a very long time, preferably up to and exceeding 1200 minutes to sorb ortho-xylene in an amount of 30% of total xylene sorption capacity. For those materials, it may be more convenient to determine the sorption time for a lower extent of sorption, such as 5%, 10% or 20% of capacity, and then to estimate the 30% sorption time by applying the following multiplication factor, F, as illustrated for 5% sorption:

$$t_{0.3} = F \cdot t_{0.05}$$

| Percent of sorption capacity | Factor, F, to estimate 30% sorption time, $t_{0.3}$ |
|---|---|
| 5 | 36 |
| 10 | 9 |
| 20 | 2.25 |

Alternatively, $t_{0.3}$ may be calculated for other sorption times at less than 30% of xylene capacity using the following relationship:

$$t_{0.3} = \left(\frac{0.3}{0.x}\right)^2 (t_{0.x})$$

where $t_{0.3}$—sorption time for 30% of total xylene capacity $t_{0.x}$—sorption time for x % of total xylene capacity 0.x—fractional amount of ortho-xylene sorption to total xylene capacity In accordance with the invention, the crystalline molecular sieve component of the catalyst that is effective for the toluene conversion may have a $t_{0.3}$ value (in minutes) for ortho-xylene in excess of about 50, e.g., greater than about 200, e.g., greater than about 1200 minutes.

Toluene Disproportionation

The first catalyst can be contacted with a toluene feedstock under conditions for effecting disproportionation. Conditions effective for accomplishing high p-xylene selectivity and acceptable toluene conversion levels include a reactor inlet temperature of from about 200° C. (392 F.) to about 550° C. (1022 F.), preferably from about 312° C. (600 F.) to about 532° C. (1000 F.); a pressure from about atmospheric to about 5000 psi, preferably about 20 to about 1000 psig; a WHSV from about 0.1 to about 20, preferably from about 0.5 to about 10; and a $H_2$/hydrocarbon mole ratio from about 0 to about 20, preferably from about 0 to about 10. This process may be conducted in either continuous flow, batch or fluid bed operation.

The catalyst can be further modified to reduce undesirable amounts of by-products, particularly ethylbenzene, by incorporating a hydrogenation/dehydrogenation function within the catalyst, such as by the addition of a metal compound such as platinum or other metals of Groups 4 to 13 of the Periodic Table, such as platinum, palladium, silver, gold, copper, zinc, nickel, gallium, cobalt, molybdenum, rhodium, ruthenium, manganese, rhenium, tungsten, chromium, iridium, osmium, iron, cadmium, and mixtures (combinations) thereof. The metal may be added by cation exchange or by impregnation by known methods in amounts of from about 0.01% to about 10%, typically about 0.05%–10%.

Toluene disproportionation over the selectivated catalyst shown selectivity toward a high-purity p- and m-xylene product. It is possible to achieve a xylene product with virtually no o-xylene at toluene conversation levels as high as 27%. A $C_8$ stream can be produced with no o-xylene, blended to reduce o-xylene, or a stream can be taken through a o-xylene splitter to prepare a $C_8$ feed to a purified terephthalic acid unit. The xylene product preferable includes essentially no o-xylene or negligible o-xylene. By negligible is meant less than 0.2%, preferably less than 0.1%, more preferably less than 0.05%.

Terephthalic Acid Production

A number of processes are used commercially in the production of terephthalic acid. One is the Amoco process described, e.g., in U.S. Pat. No. 2,833,816. This process involves liquid phase air oxidation of p-xylene using multivalent (heavy) metals, particularly cobalt and manganese as catalyst in an acetic acid solvent and with bromine as a renewable source of free radicals. The terephthalic acid product crystals are recovered, e.g., by centrifugation, and purified by dissolving the crystals in water contacting with a hydrogenation catalyst, e.g., noble metal on a carbon support, and again recovering the crystals. Dimethyl terephthalate can be produced by liquid phase esterification of the terephthalic acid using metal catalysts such as zinc, molybdenum, antimony and tin with a large excess of methanol.

In another process, four steps are used, alternating oxidation and esterification to produce dimethyl terephthalate, as described, e.g., in British Patent Specification Nos. 727,989 and 809,730. First, p-xylene is oxidized with a molecular oxygen-containing gas (air) in a liquid phase in the presence of a heavy metal catalyst such as cobalt, manganese, or mixture of both to produce p-toluic acid (PTA) which is esterified with methanol to produce methyl p-toluate (MPT). A second oxidation of the MPT with the same catalyst and molecular oxygen yields in a liquid phase yields monomethyl terephthalate which is esterified to the diester dimethyl terephthalate.

Both terephthalic acid and dimethyl terephthalate are used in the production of polyethylene terephthalate (PET) or other polyesters through a reaction with glycol, e.g., ethylene glycol or tetramethylene glycol.

The invention is illustrated by the following non-limiting examples.

EXAMPLE

A catalyst was manufactured by multiple silica selectivation of a ZSM-5 containing extrudate (65% zeolite/35% silica). Selectivation of the catalyst was carried out using the pore filling technique contacting the catalyst four times with 7.8% organosilicone fluid (Dow-550, Dow Chemical Co., Midland, Mich.) dissolved in decane and twice more with 2% organosilicone fluid, followed by hybrid calcination in nitrogen/air.

Catalyst evaluations were performed by loading 2 g of extrudate, mixed with sand as a packing material, into a ⅜" OD reactor tube. The catalyst was then heated to reaction temperature under nitrogen, at which time, a mixed hydrogen/toluene feed is introduced. Sample analyses were acquired via on-line gas chromatography (GC). Operating conditions and yields are shown below in Table 1.

TABLE 1

| | | | | | |
|---|---|---|---|---|---|
| Temp (F.) | 734 | 752 | 769 | 787 | 805 |
| Press (Psig) | 275 | 275 | 275 | 275 | 275 |
| WHSV | 3 | 3 | 3 | 3 | 3 |
| $H_2$/HC | 1 | 1 | 1 | 1 | 1 |
| Yields (Wt. %) | | | | | |
| C5- | 0.36 | 0.51 | 0.75 | 1.02 | 1.47 |
| Benzene | 6.79 | 7.81 | 9.64 | 11.86 | 13.71 |
| Ethylbenzene | 0.10 | 0.16 | 0.22 | 0.31 | 0.39 |
| p-xylene | 7.60 | 9.37 | 9.94 | 10.64 | 10.76 |
| m-xylene* | — | 0.09 | 0.13 | 0.17 | 0.22 |
| o-xylene* | — | — | — | — | — |
| C9+ | 0.20 | 0.26 | 0.27 | 0.32 | 0.37 |
| p-Selectivity | {100} | 99.07 | 98.70 | 98.43 | 98.04 |
| p-Purity | 98.7 | 97.40 | 96.59 | 95.68 | 94.63 |
| Toluene Conversion | 15.1 | 18.28 | 21.02 | 24.42 | 27.02 |

*Where no accurate measurement of concentration can be obtained in the present gas chromatographic technique, a value of less than 100 ppm is estimated.

An optimum level of toluene conversion is selected and a product slate is selected in which the $C_8$ fraction is essentially all p-xylene. This stream can be used directly (no crystallization or sorption process required to purify the p-xylene) to a Purified Terephthalic Acid (PTA) unit for oxidation and subsequent esterification.

We claim:

1. A process for producing terephthalic acid or dimethyl terephthalate comprising:
   (a) contacting a reaction stream comprising toluene under toluene disproportionation conditions with a first catalyst wherein the first catalyst comprises a crystalline molecular sieve which has been selectivated so as to have an ortho-xylene diffusion time of greater than 1200 minutes, said first contacting producing para-xylene product containing less than 0.2% o-xylene, and
   (b) contacting the para-xylene product of (a), without subjecting said product to an intermediate purification step, with a second catalyst under oxidizing conditions to produce terephthalic acid and/or dimethyl terephthalate.

2. The process of claim 1 wherein the first catalyst comprises an intermediate pore zeolite, a SAPO, an $ALPO_4$ or combination thereof.

3. The process of claim 2 wherein the intermediate pore zeolite has a Constraint Index ranging from 1 to 12 and a silica to alumina ratio of at least 10.

4. The process of claim 1 wherein the toluene disproportionation conditions comprise a temperature from about 600° F. to about 1000° F., a pressure from about 20 to about 1000 psi, a weight hourly space velocity (WHSV) of about 0.5 to about 20, and hydrogen/hydrocarbon mole ratio of about 0 to about 10.

5. The process of claim 1 wherein the first catalyst has been selectivated by exposure to a silicon compound or a carbon compound.

6. The process of claim 5 wherein the selectivation is ex situ silicon selectivation by impregnation or multiple impregnation, in situ silicon trim selectivation, carbon selectivation, or combinations thereof.

7. The process of claim 1 wherein the first catalyst comprises crystalline molecular sieve which is self-bound, includes a silica binder, includes a binder with no intentionally added alumina, or includes zeolite bound zeolite.

8. The process of claim 1 wherein the first catalyst comprises a crystalline molecular sieve having incorporated metal of Pt, Pd, Ag, Au, Zn, Ga, Cu, Ni, Rh, Ir, Co, Fe, Ru, Mn, Re, W, Mo, Cr or combinations thereof.

9. The process of claim 1 wherein contacting (b) comprises liquid phase oxidation.

10. The process of claim 1 wherein the para-xylene product of (a) contains less than 0.1% ortho-xylene.

* * * * *